(12) United States Patent
Putzeys

(10) Patent No.: US 12,310,628 B2
(45) Date of Patent: May 27, 2025

(54) PROXIMAL HUMERAL FIXATION PLATE AND METHOD FOR PLACING SUCH A FIXATION PLATE

(71) Applicant: BV BELTRAUM, Bellegem (BE)

(72) Inventor: Guy Putzeys, Bellegem (BE)

(73) Assignee: BV Beltraum, Bellegem (BE)

( * ) Notice: Subject to any disclaimer, the term of this patent is extended or adjusted under 35 U.S.C. 154(b) by 370 days.

(21) Appl. No.: 18/019,224

(22) PCT Filed: Aug. 2, 2021

(86) PCT No.: PCT/IB2021/057030
§ 371 (c)(1),
(2) Date: Feb. 1, 2023

(87) PCT Pub. No.: WO2022/029592
PCT Pub. Date: Feb. 10, 2022

(65) Prior Publication Data
US 2023/0270430 A1   Aug. 31, 2023

(30) Foreign Application Priority Data

Aug. 5, 2020 (BE) .................... 2020/5560

(51) Int. Cl.
*A61B 17/04* (2006.01)
*A61B 17/68* (2006.01)

(52) U.S. Cl.
CPC .......... *A61B 17/68* (2013.01); *A61B 17/0401* (2013.01)

(58) Field of Classification Search
CPC ..................................................... A61B 17/68
See application file for complete search history.

(56) References Cited

U.S. PATENT DOCUMENTS

| 6,960,213 B2 * | 11/2005 | Chervitz | A61B 17/82 |
| | | | 606/103 |
| 9,526,544 B1 | 12/2016 | Kumar | |
| 2005/0182406 A1 * | 8/2005 | Orbay | A61B 17/8047 |
| | | | 606/232 |

(Continued)

FOREIGN PATENT DOCUMENTS

| DE | 102005043281 | 3/2007 |
| GB | 2471290 | 12/2010 |

(Continued)

*Primary Examiner* — Christian A Sevilla
(74) *Attorney, Agent, or Firm* — Davis, Malm & D'Agostine, P.C.; Richard L. Sampson

(57) ABSTRACT

The invention concerns a fixation plate for fixing to a proximal humerus, comprising a head part for attachment distally from the foot plate of the major tubercle of the humerus, which is provided with first screw holes with internal screw thread for angularly stable screws, of which two arranged furthest from the shaft part are provided as upper screw holes for a downwardly directed screw, and suture holes, of which one anchoring suture hole for anchoring thereto, by means of suture material, a bone anchoring element attached in the apex of the humeral head, and a shaft part adjoining this head part at the bottom for being attached to the humeral shaft. In addition, the invention concerns a set of such a fixation plate and a side arm, and a method for treating a shoulder fracture using such a fixation plate.

14 Claims, 9 Drawing Sheets

(56) References Cited

U.S. PATENT DOCUMENTS

| | | | |
|---|---|---|---|
| 2006/0189987 A1* | 8/2006 | Orbay | A61B 17/8888 |
| | | | 606/62 |
| 2006/0235402 A1 | 10/2006 | Celli | |
| 2007/0270849 A1* | 11/2007 | Orbay | A61B 17/74 |
| | | | 606/291 |
| 2012/0179208 A1 | 7/2012 | Geissler | |
| 2014/0194907 A1 | 7/2014 | Bonutti | |
| 2015/0051601 A1 | 2/2015 | Larsen | |
| 2016/0100932 A1* | 4/2016 | Kumar | A61F 2/0811 |
| | | | 606/281 |
| 2016/0166297 A1 | 6/2016 | Mighell | |
| 2016/0287297 A1 | 10/2016 | Geissler | |
| 2018/0000496 A1 | 1/2018 | Langdale | |

FOREIGN PATENT DOCUMENTS

| | | |
|---|---|---|
| WO | 2005072285 | 8/2005 |
| WO | 2014110421 | 7/2014 |
| WO | 2022029592 | 2/2022 |

* cited by examiner

PROXIMAL HUMERAL FIXATION PLATE AND METHOD FOR PLACING SUCH A FIXATION PLATE

The invention concerns a fixation plate for fixing to a proximal humerus, comprising a head part and a shaft part adjoining the head part at the bottom, wherein the head part is designed to be attached distally from the footplate of the major tubercle of the humerus, and for this purpose is provided with:
- first screw holes for insertion of angularly stable screws therein; and
- suture holes for insertion of suture material therein; and
  where the shaft part is designed to be attached to the humeral shaft and for this purpose is provided with second screw holes for insertion of fixing screws therein.

Such fixation plates are used for treating shoulder fractures.

Examples of such fixation plates are described and depicted in WO 2005/072285 A2, US 2012/0179208 A1, US 2006/0235402 A1, WO 2014/110421 A1, US 2018/0000496 A1, US 2016/0287297 A1 DE 10 2005 0743 281 A1, US 2016/0166297 A1 and U.S. Pat. No. 9,526,544 B1.

In certain shoulder fractures, a fixation plate is attached to the proximal humerus. The shaft part of the fixation plate here comprises said second screw holes for fixing this shaft part to the humeral shaft. One or more of these second screw holes may be elongated and be at least partially provided with an internal screw thread and/or be at least partially free from an internal screw thread.

The head part contains said first screw holes which are provided with an internal screw thread for insertion of angularly stable screws.

In order to further reinforce the construction of the fixation plate to the humerus, typically suture threads as sutures are pulled through the tendons around the humeral head and fixed to the fixation plate via said suture holes, which for this purpose are typically arranged on the edge of the fixation plate.

Despite these well-developed fixation systems, there are a number of significant complications in the operative techniques in which these fixation plates are used.

A first example of such a complication is the tilting back of the humeral head after the operation, wherein the fixation plate cannot prevent this tilting.

A second example of such a complication is the progressive settling of the humeral head over the screws, whereby perforation of the screw ends of the humeral head screws through the joint surface occurs. This leads to possible destruction of the joint.

These complications mainly occur in elderly people, where the screws have less of a grip in the weaker bone of these elderly people.

The problem of the known operative techniques with the known fixation plates is described for example in Jonathan Barlow et al, Locking plate fixation of proximal humerus fractures in patients older than 60 years continues to be associated with a high complication rate, J Shoulder Elbow Surg (2020) 29, 1689-1694.

The object of this invention is to provide a proximal humeral fixation plate, a set and a method with which said complications can be limited.

This object of the invention is achieved by providing a fixation plate comprising a head part and a shaft part adjoining the head part at the bottom, wherein the head part is designed to be attached distally from the foot plate of the major tubercle of the humerus, and for this purpose is provided with:
- first screw holes with internal screw thread for insertion of angularly stable screws therein; and
- suture holes for insertion of suture material, wherein one of the suture holes is provided as an anchoring suture hole for anchoring thereto, by means of suture material, a bone anchoring element attached in the apex of the humerus humeral head, wherein two first screw holes arranged furthest from the shaft part are provided as upper screw holes for insertion therein of a downwardly directed screw;
- and wherein the shaft part is designed to be attached to the humeral shaft and for this purpose is providing second screw holes for insertion of fixing screws.

Together with said angularly stable screws, fixing screws, suture material and bone anchoring element, a fixation plate forms a proximal humeral fixation system.

The terms upward, downward, horizontal and vertical are used with respect to the fixation plate viewed in a position of said fixation plate in which said fixation plate is typically mounted on a humerus, viewed with respect to a standing person with the corresponding arm hanging down.

A vertical plane here substantially corresponds to a plane in which the shaft part mainly extends, and substantially coincides with an ideal support surface of the shaft part against the humeral shaft.

A horizontal plane extends substantially transversely to the shaft part, transversely with respect to such a vertical plane.

A downwardly directed screw is a screw which, when screwed in with its starting point leaving from a horizontal plane, is always screwed further below this horizontal plane so that its starting point sits furthest below the horizontal plane. The screw thus forms a downward angle with respect to said horizontal plane.

An upwardly directed screw is a screw which, when screwed in with its starting point leaving from a horizontal plane, is always screwed further above this horizontal plane so that its starting point sits furthest above the horizontal plane. The screw thus forms an upward angle with respect to said horizontal plane.

A said bone anchoring element is known and implemented in various embodiments. It is typically mounted on an inserter. The bone anchoring element here typically engages securely into the bone and engages below the subchondral bone. Such bone anchoring elements are known for example in the form of a screw or wedge or thread which winds into a knot etc. In the various possible embodiments, the bone anchoring element always attaches into the bone as a barb. The anchor is subchondrally attached medially from the tendon insertion site, making a minimal hole in the cartilage. This hole is kept as small as possible by limiting the size of the bone anchoring element. Such a bone anchoring element is provided with the necessary suture material for securing this. Once the bone anchoring element has been arranged in the apex of the humerus, the suture material is guided through the supra- and infraspinatus tendon insertion and secured to the anchoring suture hole.

Conventionally, suture material which secures the fixation plate is arranged in the tendons around the humeral head. According to the invention, now a bone anchoring element is provided which can be secured in the bone of the humeral head and then sutured to the fixation plate. In this way, tilting of the humeral head can be better avoided.

In the prior art, the risk of screw perforation is greatest for the most proximal angularly stable screws. According to the invention, it is now provided to point these two or more, proximal, angularly stable screws atypically downward in order to also reinforce the calcar. This also avoids the screws perforating the joint face. Also, as in the prior art, further angularly stable screws may be provided to reach the calcar from a horizontal or inferior position.

In a preferred embodiment, the anchoring suture hole is provided for adjustably arranging suture material therein.

By ensuring that suture material can be adjustably inserted in the anchoring suture hole, this suture material can be attached in a more controllable fashion.

In a specific embodiment, the anchoring suture hole of a fixation plate according to this invention may comprise a tunnel-like cavity, through which the suture material can be inserted, and the fixation plate may be provided with adjustment means for adjustably securing the suture material in the tunnel-like cavity.

Thus for example, a screw hole may be provided in the fixation plate which opens in the tunnel-like cavity for adjustably securing, by means of a setscrew, the suture material in the tunnel-like cavity. This fixation plate may here be provided in a set which also contains a setscrew which can be inserted in the screw hole for adjustably securing the suture material in this tunnel-like cavity.

Alternatively, for example a bayonet system or an eccentric system may be provided for adjustably securing suture material in such a tunnel-like cavity.

The anchoring suture hole is furthermore preferably provided for releasably arranging the suture material therein, so that this suture material can be arranged in the anchoring suture cavity in a reversible fashion.

The anchoring suture hole is preferably arranged centrally in the head part. More specifically, this anchoring suture hole preferably comprises a tunnel-like cavity with a first inlet opening which opens centrally at an upper edge of the fixation plate, and a second inlet opening which opens centrally in the head part of the fixation plate. A screw hole for said setscrew is then preferably provided centrally between these two inlet openings in the head part and here opens in the tunnel-like cavity.

Two types of screw holes for angularly stable screws are known.

A first type concerns screw holes with which an angularly stable screw can be arranged variably and adjustably, wherein the angle can typically be adjusted by maximum 15° in each direction.

A second type concerns screw holes with which the angularly stable screw can only be arranged at one specific, fixed angle.

In order to produce said upper screw holes of a fixation plate according to this invention, in principle both types of screw holes may be used. Preferably however, these upper screw holes are designed according to the second said type. The benefit of a variable angularly stable screw does not actually offset the high production cost. Such variable angularly stable screws may also be less reliable. Thus there is a risk of collision, wherein on insertion of a first variable angularly stable screw, the precise location thereof is not known sufficiently precisely, and when drilling a screw hole for a next screw to be inserted, the screw already inserted may be touched. The drill may be damaged and even break. Another disadvantage is that a second path must be drilled in the case of collision.

The internal screw thread of each of the two or more upper screw holes preferably has a longitudinal axis which is arranged at a downward angle between 10° and 35°, more preferably between 15° and 25°, and even more preferably between 15° and 20° relative to a horizontal plane. Even more preferably, this angle amounts to around 16°.

This downward angle is provided to ensure that the most proximal screws can reach with certainty as optimally as possible the calcar.

The two or more upper screw holes are further preferably each provided with a second internal screw thread which comprises a second longitudinal axis which is arranged at an upward angle of between 10° and 35°, preferably between 15° and 25°, and more preferably between 20° and 25° with respect to the horizontal plane. Even more preferably, this angle amounts to around 24°.

When the upper screw holes are provided with both a first said internal screw thread and a second internal screw thread, this same fixation plate may be used both in operations where there is a risk for said complications, so that the most proximal screws can be directed downward to avoid these complications, and also in operations where these complications are not expected and the most proximal screws can be directed upward in the conventional way.

Said internal screw threads are preferably configured in a conically converging fashion.

In a particularly preferred embodiment, the two or more upper screw holes are each designed substantially in a figure-of-eight form with a upper inlet opening and a lower inlet opening, wherein the upper inlet opening is provided with the first said internal screw thread, and the lower inlet opening is provided with the second internal screw thread. In some cases, conversely, the upper inlet opening may be provided with the second internal screw thread and the lower inlet opening with the first internal screw thread.

The object of this invention is furthermore achieved by providing a set of a fixation plate according to this invention and a side arm which is releasably attachable to the head part and is provided with a second anchoring suture hole, in order to anchor the side arm medially from the minor tubercle by means of suture material and a second bone anchoring element.

The side arm here bridges the bicipital groove and projects over the medial edge of the bicipital groove. The bicipital tendon situated in the bicipital groove is left unobstructed. In some cases, the side arm may also end above the bicipital groove as long as there is no conflict between the suture thread and the bicipital tendon.

The side arm is preferably provided with only one said anchoring suture hole. This side arm is here provided for fixing suture material thereto, such as typically suture thread, and is here preferably designed minimally to perform this function.

The second anchoring suture hole may be provided in a similar fashion to the above-mentioned anchoring suture hole in the head part of the fixation plate. This second anchoring suture hole is also preferably designed for adjustable insertion of the suture material therein.

The side arm may be attached either at the front of the fixation plate or at the back of this fixation plate.

The side arm is preferably provided with a fixing body for fixing said side arm to the head part.

More specifically, the fixation plate may be provided with a recess in its head part in which the fixing body may be arranged for fixing the fixing body to the head part.

Preferably, the side arm is designed symmetrically, so that this can be attached firstly at a first upright side, protruding with respect to the fixation plate, and also twisted through 180° at a second upright side, protruding with respect to the fixation plate. In this way, a same side arm may be used both for treating a shoulder fracture on a left shoulder and for treating a shoulder fracture on a right shoulder. Preferably, the fixation plate is provided with a corresponding said recess on each of the upright sides. Alternatively or additionally, the fixing body may be provided for extending over the complete width of the head part.

More specifically, the fixing body may be provided with attachment pins which can be inserted in said suture holes of the head part which are configured as attachment holes, for fixing the fixing body to the head part. Even more specifically, the fixing body may be provided with one or more fixing screw holes, and the head part may be provided with one or more corresponding fixing screw holes, for fixing the fixing body to the head part by means of one or more fixing screws. When the fixing body extends over the complete width of the head part, such fixing screw holes in the head part for example may be more specifically provided at opposite side edges of the head part, so that the fixing body is arranged over the head part and attached on both sides of said head part.

In a particular embodiment, the side arm can be height-adjustably attached to the fixation plate.

An above-mentioned second bone anchoring element and an above-mentioned side arm may also be beneficial in fixation plates according to the prior art, in which the upper screw holes are not provided for insertion of a downwardly directed screw therein. They may also be useful in fixation systems which are not provided with a first said bone anchoring element and anchoring suture hole in the head part of the fixation plate.

On the side away from the head part, the shaft part of the fixation plate according to this invention is preferably provided with an edge which is designed concave so as to form a free cavity centrally below the shaft part.

The concave design of this end limits to a minimum conflicts with the tendon insertion site which is located there, so that if necessary also only a minimum of tendon need be disinserted in order to position the fixation plate. The end thus acts as a rougine with which the deltoid tendon can be disinserted to the maximum necessary. This contrasts with the present method in which firstly disinsertion takes place with a separate rougine and then the plate is attached. With a suitable end, this phase is avoided and less disinsertion is required, since the fixation plate can be designed shorter than the existing fixation plates.

Such a concave end may also be beneficial in fixation plates according to the prior art in which the upper screw holes are not provided for insertion therein of a downwardly directing screw, and in fixation systems which are not provided with an afore-mentioned bone anchoring element and an anchoring suture hole in the fixation plate.

Preferably, in the shaft part of a fixation plate according to this invention, at least one screw hole is formed as a slot in the shaft part. Such a slotted screw hole allows a first fixing screw to be inserted and then if necessary the fixation plate can be positioned more precisely with respect to the humerus.

The screw holes in the shaft part are further preferably staggered with respect to one another. These screw holes are then not arranged on one vertical line above one another, but at least partially offset with respect to this vertical line. In this way, the shaft part can be firmly attached to the humeral shaft without the shaft beginning to split.

The invention will now be explained in more detail with reference to the following detailed description of some embodiments of proximal humeral fixation systems with fixation plates and methods according to this invention. The aim of this description is exclusively to give clarifying examples and to indicate further advantages and features of this invention, and it may therefore in no way be interpreted as a restriction of the area of application of the invention or of the patent rights claimed in the claims.

In this detailed description, by means of reference signs, reference is made to the appended drawings in which.

Figure 1:
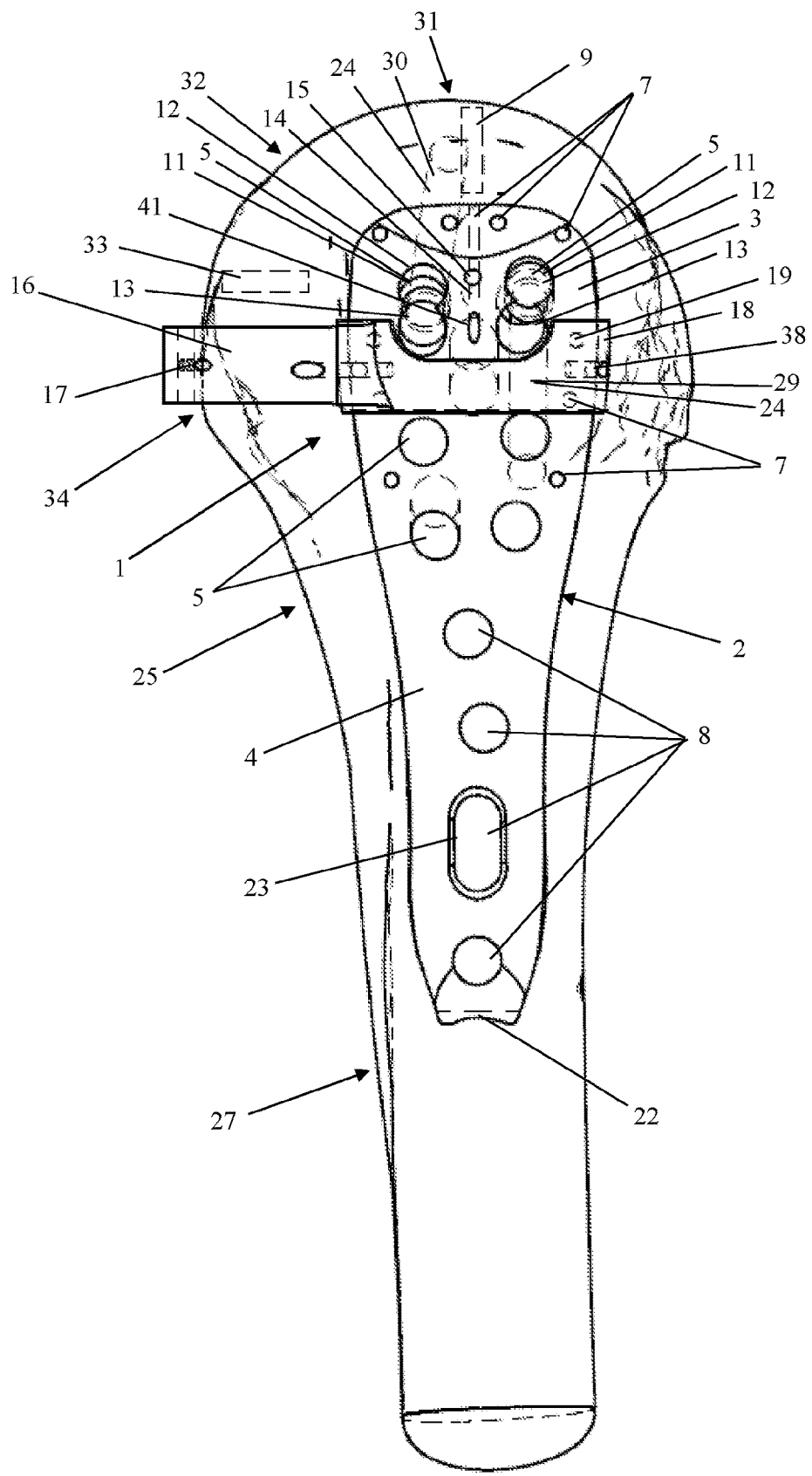
FIG. 1 shows a fixation system according to this invention attached to a humerus, in front view.

The proximal humoral fixation systems (1) illustrated comprise a fixation plate (2), a side arm (16) which can be releasably attached thereto, bone anchoring elements (9, 33), screws (24, 35), and suture material (28).

The fixation plate (2) also comprises a head part (3) and a shaft part (4) adjoining this head part (3) at the bottom.

Figure 2:
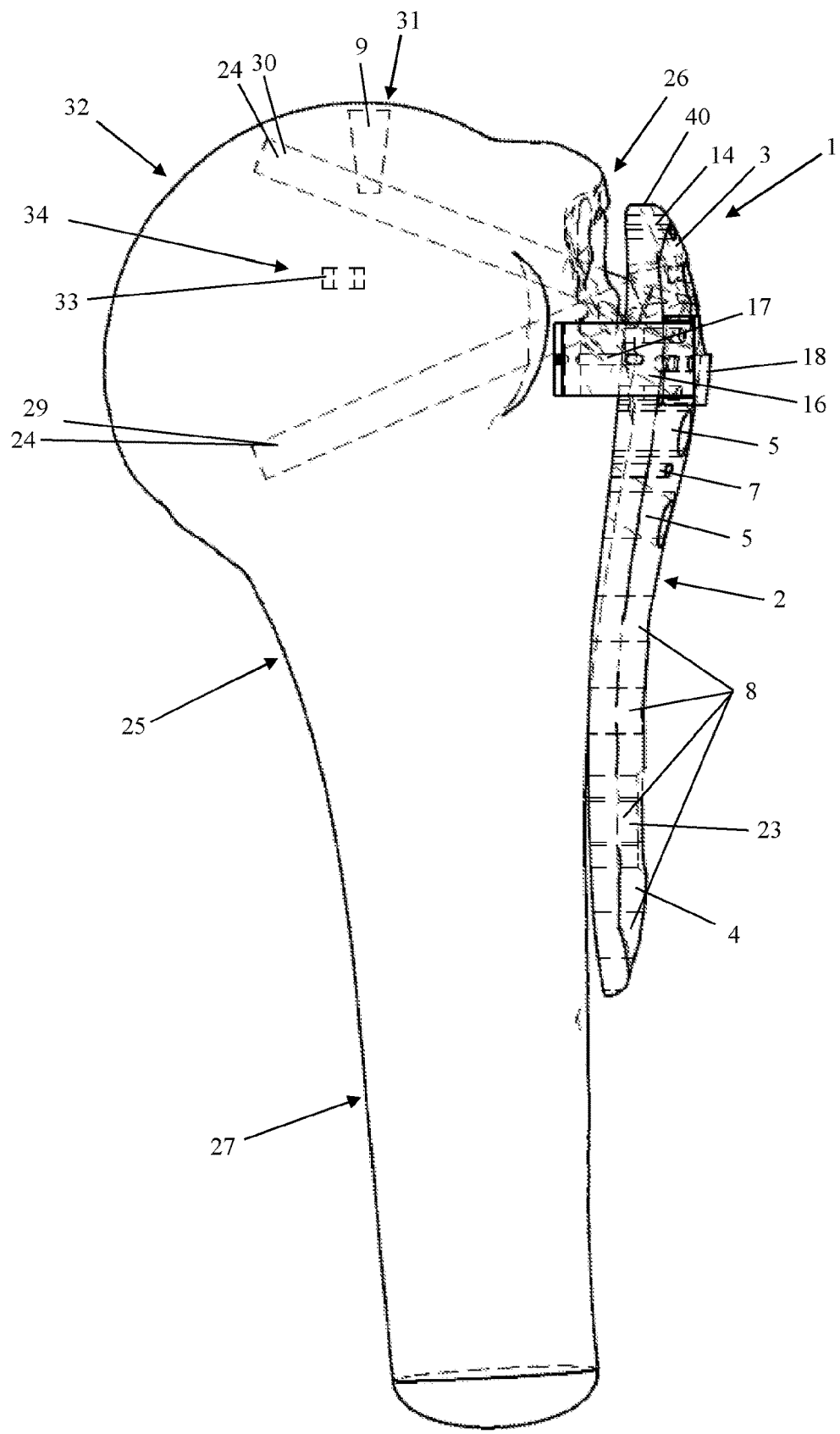
FIG. 2 shows the fixation system and the humerus from FIG. 1 in side view.
Figure 3:
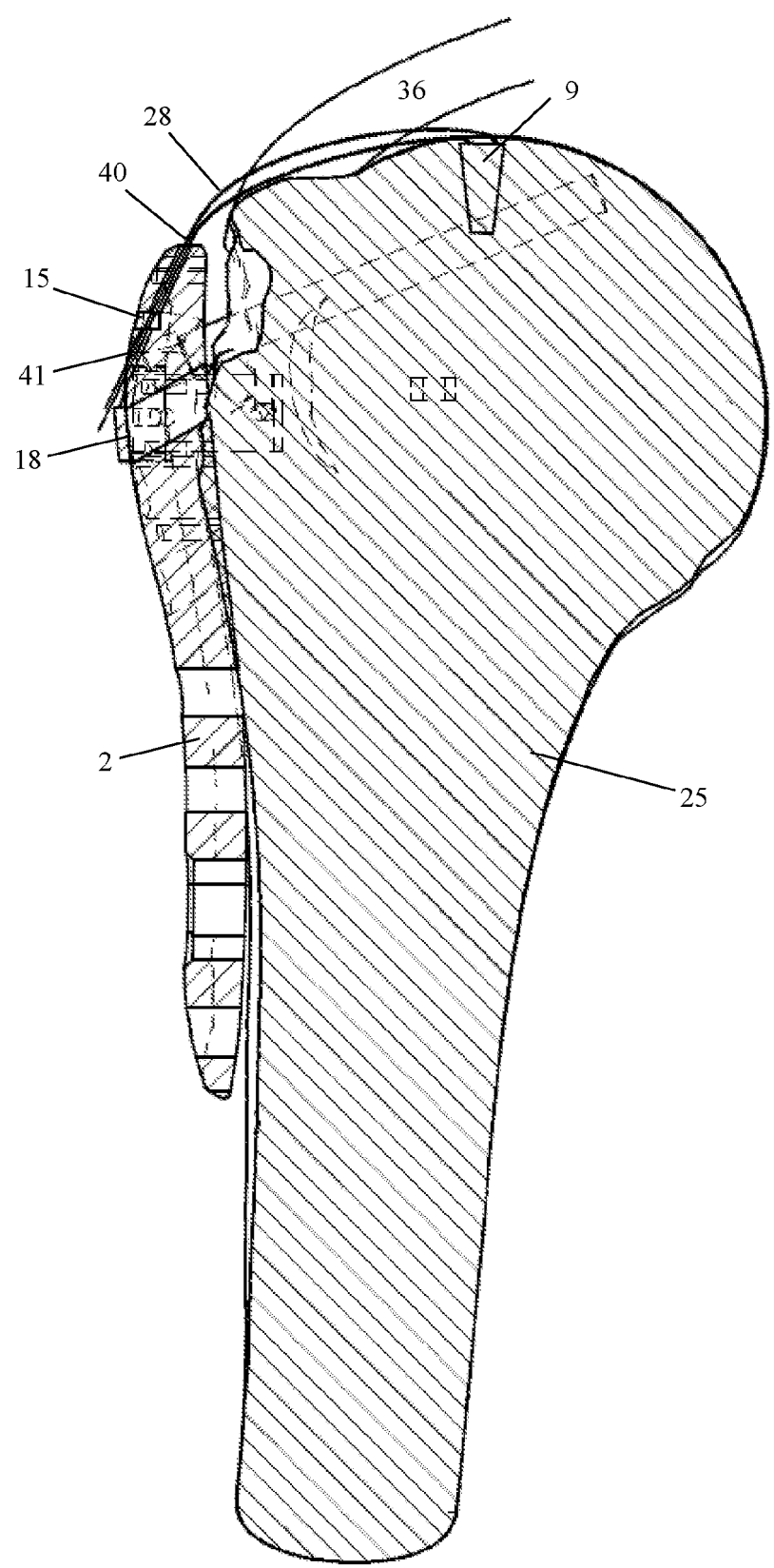
FIG. 3 shows the fixation system and the humerus from FIG. 1 in a longitudinal cross section, cut through the humerus and centrally through the fixation plate.
Figure 4:
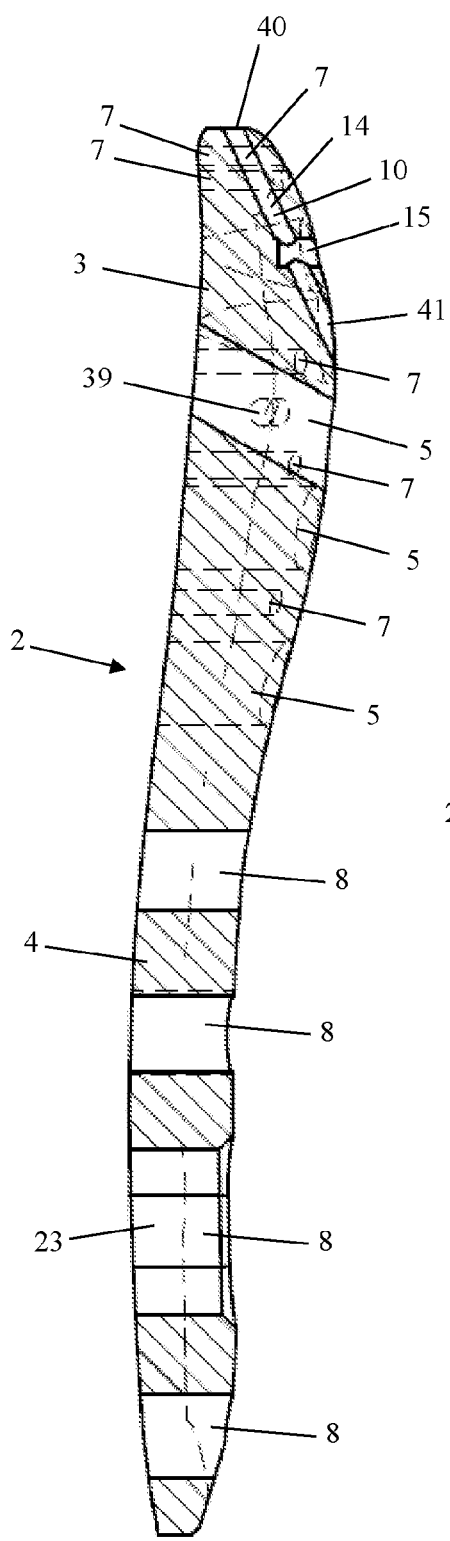
FIG. 4 shows the fixation plate of the fixation system from FIG. 1 separately in longitudinal section.

As can be seen from FIGS. 1 to 3, the shaft part (4) is designed to be attached to the humeral shaft (27).

Figure 5:
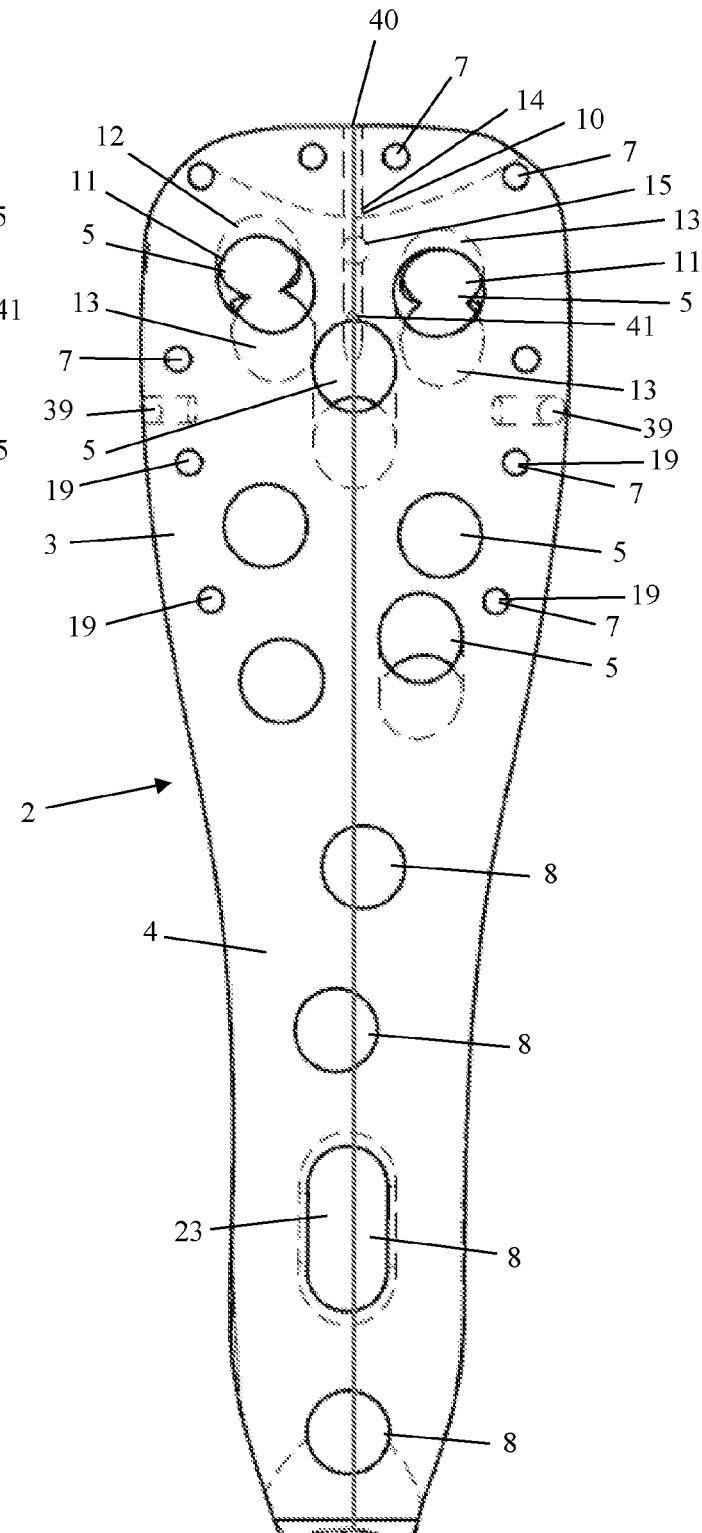
FIG. 5 shows the fixation plate of the fixation system from FIG. 1 separately in a rear view.

For this purpose, in each case several screw holes (8) are provided in the shaft part (4), for insertion of fixing screws (35) therein. The insertion of such fixing screws (35) is known from the prior art and is illustrated in the second embodiment. A centrally arranged screw hole (23) is here configured elongate so that a first fixing screw (35) may be arranged therein and still allow some play of the fixation plate (2) with respect to the humerus (25). Thus the fixation plate (2) may then if necessary be positioned more precisely with respect to the humerus (25) before any further screws (35) are inserted in further screw holes (8) in the shaft part (4). These screw holes (8) may furthermore be designed similarly to the screw holes in shaft parts of fixation plates according to the prior art. As can be seen more clearly from FIG. 5, the screw holes (8) are not arranged in a line but these are offset with respect to a vertical line. In this way, several fixing screws (35) may be arranged above one another without splitting the humeral shaft (27).

On its side facing away from the head part (3), the shaft part (4) is also provided with an edge (22) which is designed concave so that a free cavity is formed centrally below the shaft part (4), which opens towards the rear side of the fixation plate (2) and preferably extends transversely to the shaft part (4). The application of the fixation plate (2) on the humerus is hindered as little as possible by the tendon insertion present there. Fixation plates according to the prior art may equally well be provided with such a concave end in order to ensure that only a minimum of tendon need be detached in order to be able to apply the fixation plate.

The head part (3) of the fixation plates (2) depicted is designed to be attached just distally from the foot plate of the major tubercle (26), as can be seen in FIGS. 1 to 3. The head part (3) may thus be applied around 5 to 7 mm distally from the foot plate. For this purpose, several screw holes (5) are provided in the head part (3) for insertion of angularly stable screws (24) therein.

Figure 6:
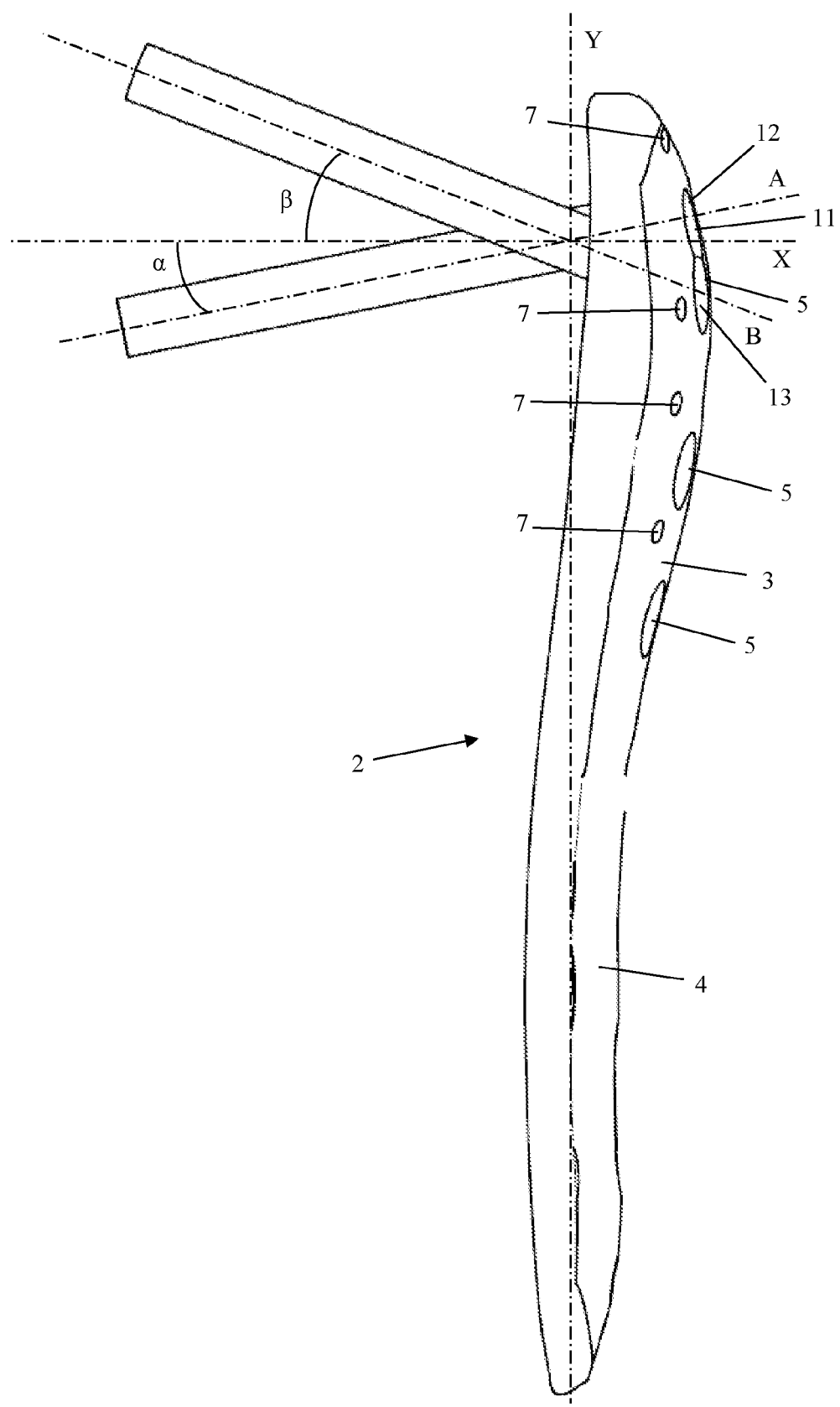
FIG. 6 shows the fixation plate of the fixation system from FIG. 1 with angularly stable screws inserted in the upper screw holes, in side view.
Figure 7:
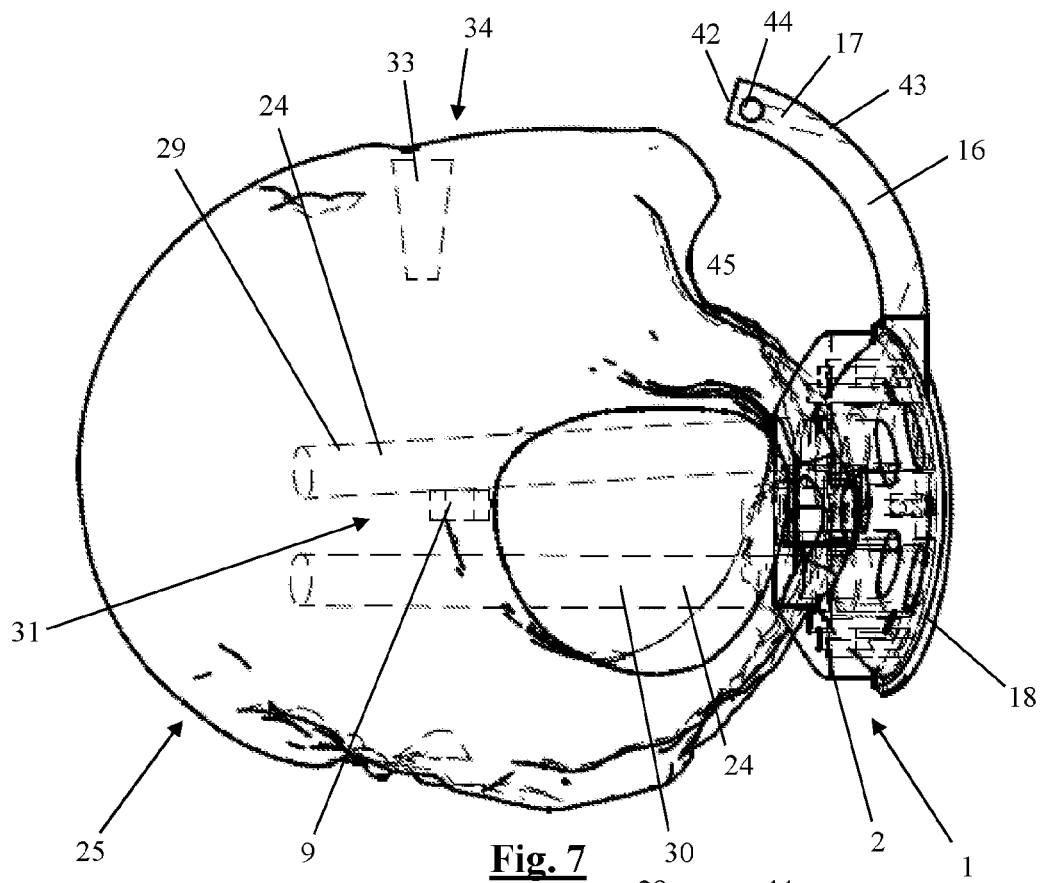
FIG. 7 shows the fixation system and the humerus from FIG. 1 in top view.
Figure 8:
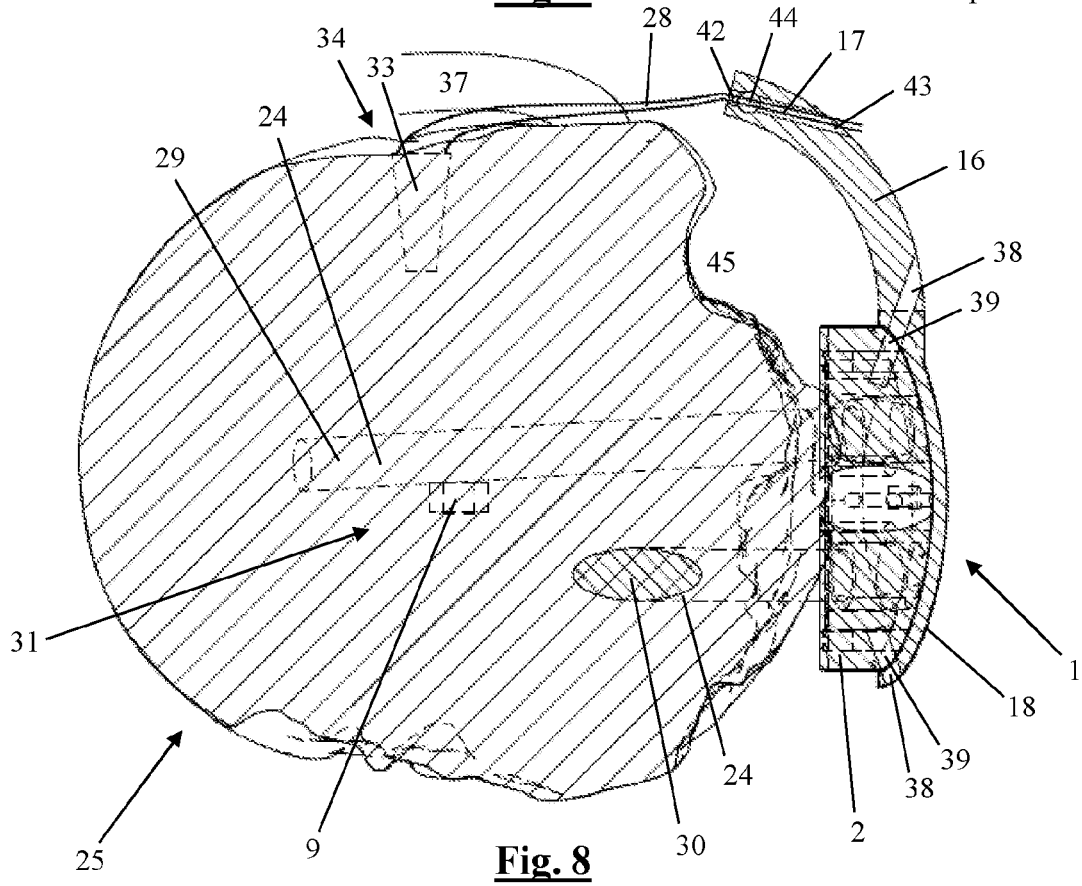
FIG. 8 shows a fixation system and the humerus from FIG. 1 in cross-section, cut centrally through the side arm.
Figure 9:
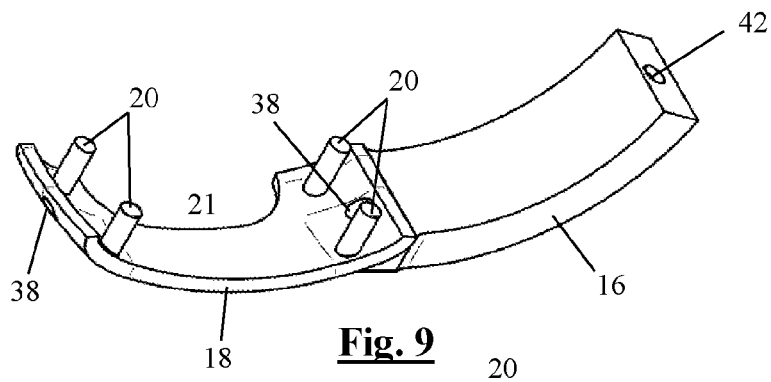
FIG. 9 shows the side arm of the fixation system from FIG. 1 separately in perspective.
Figure 10:
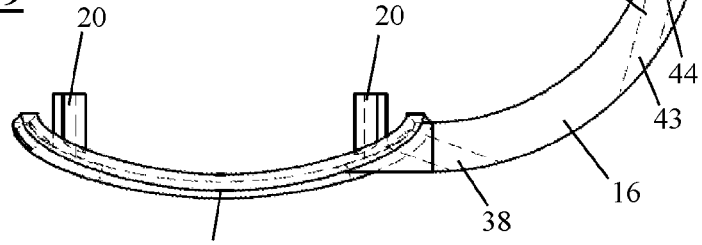
FIG. 10 shows the side arm of the fixation system from FIG. 1 separately in top view.
Figure 11:
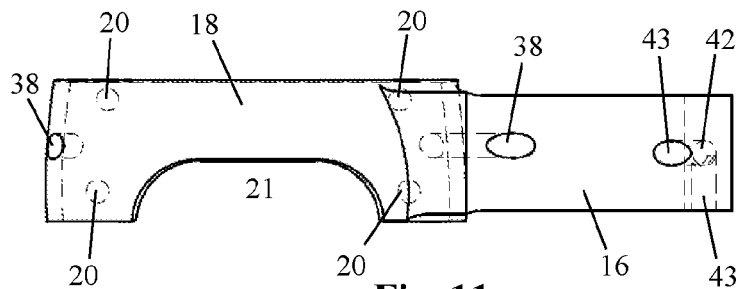
FIG. 11 shows the side arm of the fixation system from FIG. 1 separately in front view.
Figure 12:
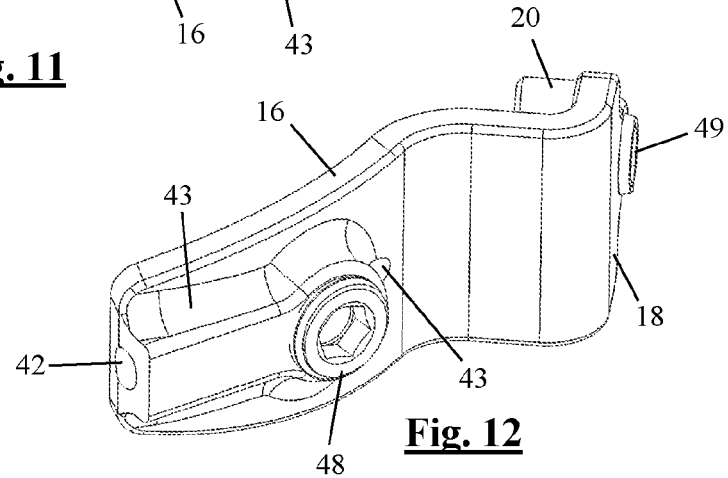
FIG. 12 shows a second embodiment of a side arm from the fixation system from FIG. 14 separately, in perspective from the left side.
Figure 13:
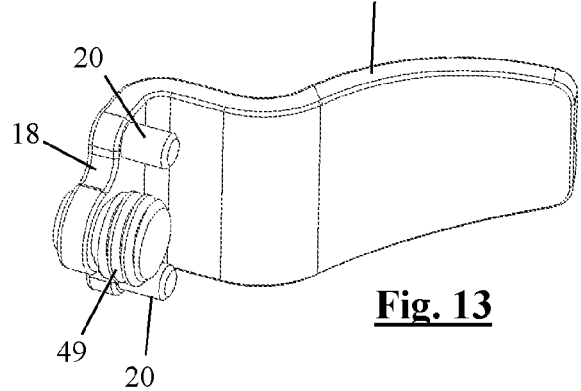
FIG. 13 shows the side arm from FIG. 12 in perspective from the rear.

The two most proximal screw holes (11) are configured in a figure-of-eight shape and are provided with the upper inlet opening (12) and a lower inlet opening (23). The upper inlet opening (12) is provided with a first internal screw thread which has a first longitudinal axis (A) which is arranged at a downward angle (a) of around 16° with respect to the horizontal plane (X), as can be seen in FIG. 6. The lower inlet opening (13) is provided with a second internal screw thread having a second longitudinal axis (B) which is arranged at an upward angle (B) of around 24° with respect to the horizontal plane (X), as can be seen in FIG. 6.

The horizontal plane (X) is arranged transversely to the vertical plane (Y) which substantially corresponds to the plane in which the shaft part (4) mainly extends and which substantially coincides with an ideal support plane of the shaft part (4) on the humeral shaft (27).

Figure 14:
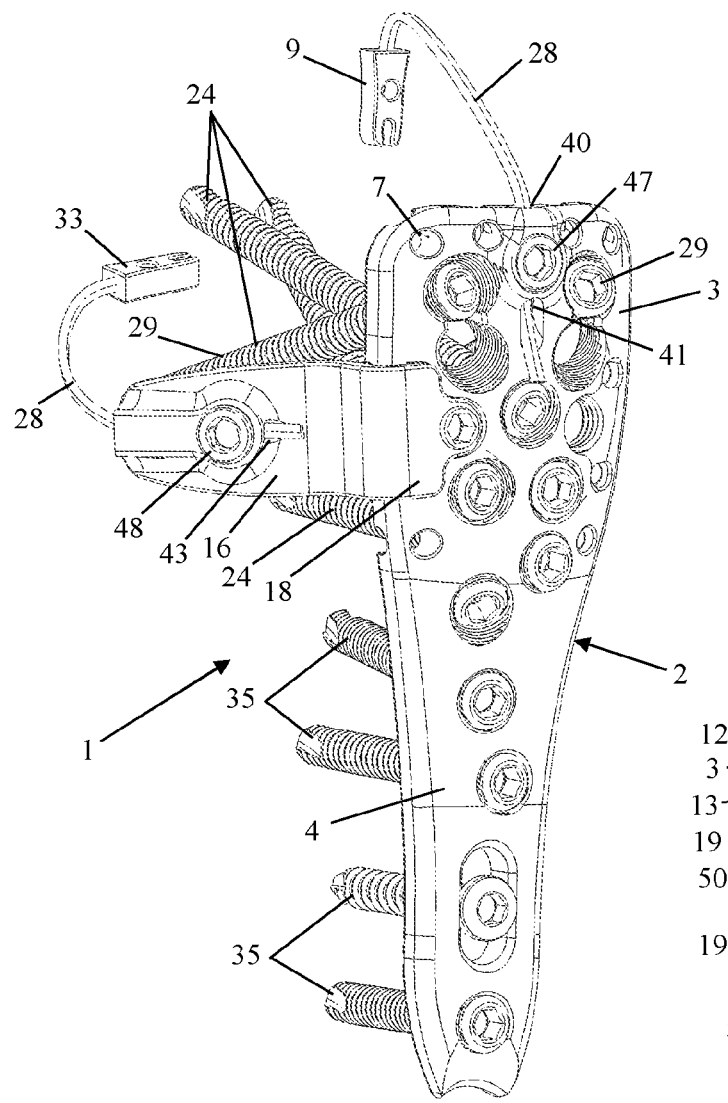
FIG. 14 shows a second embodiment of a fixation system according to this invention, in perspective from the front left.
Figure 15:
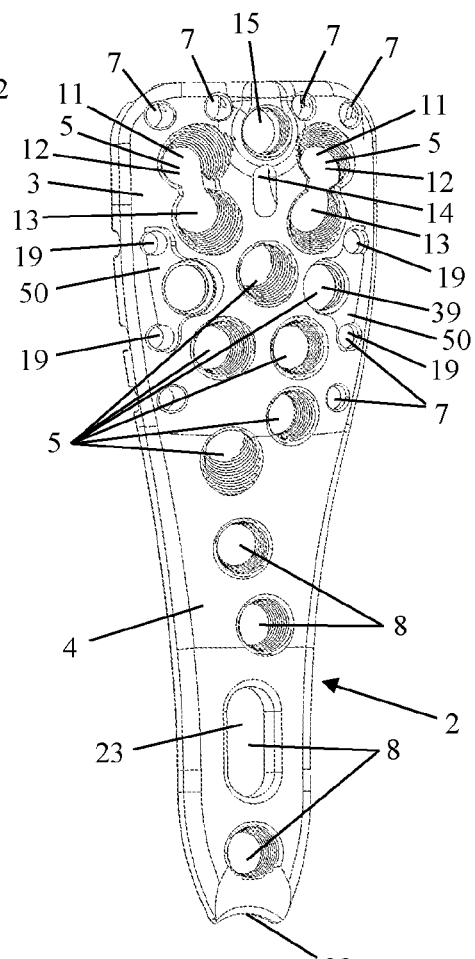
FIG. 15 shows the fixation plate from the fixation system from FIG. 14 separately, in perspective from the front.
Figure 16:
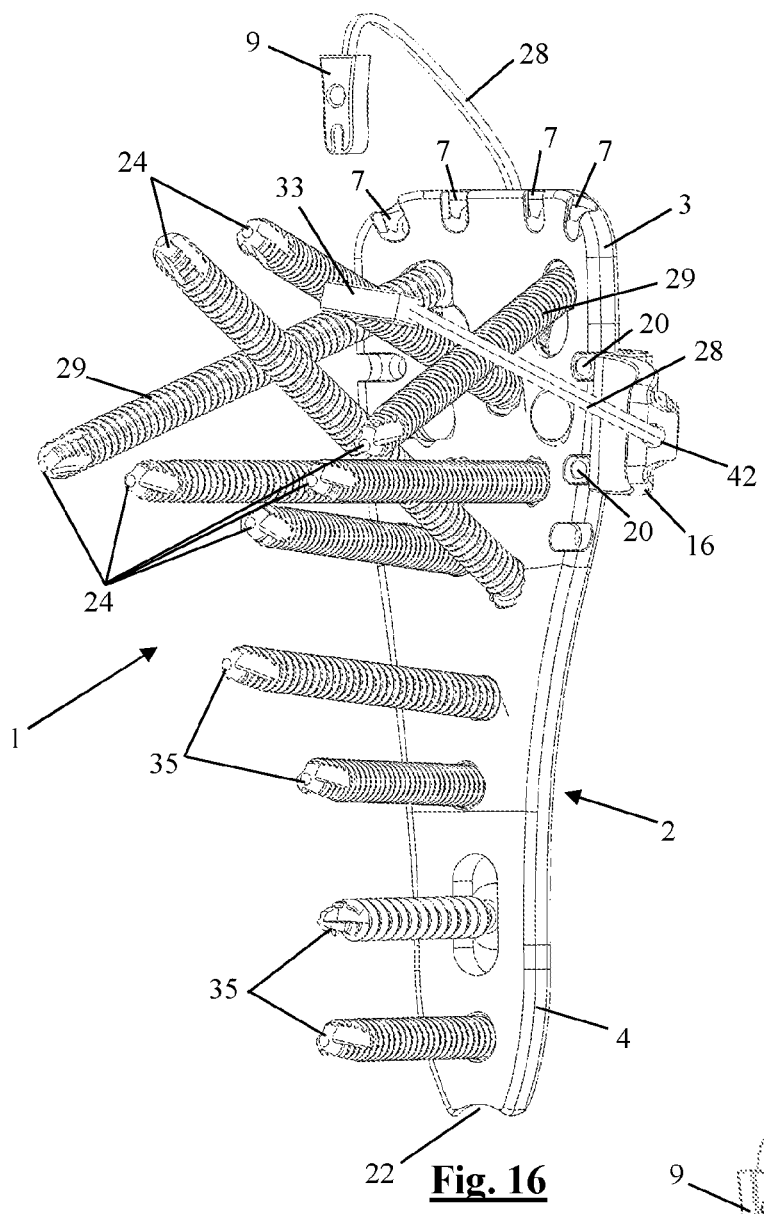
FIG. 16 shows the fixation system from FIG. 14 in perspective from the left rear.
Figure 17:
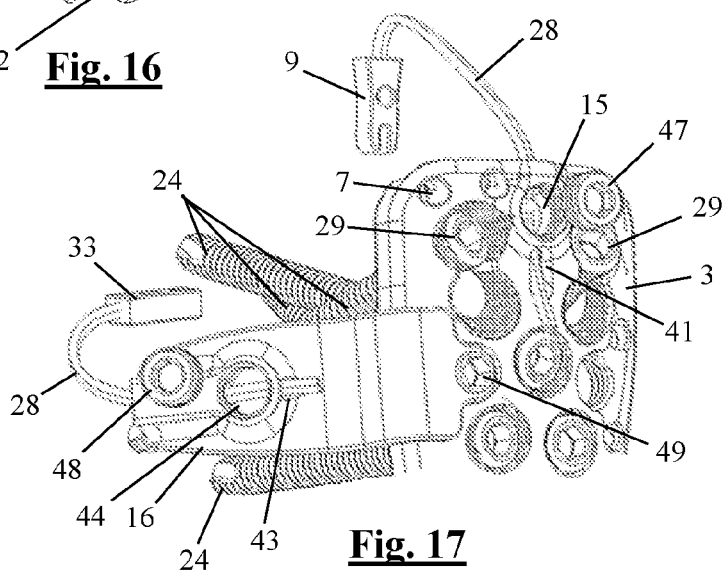
FIG. 17 shows a part of the fixation system from FIG. 14 at the level of the head part, in exploded state.

FIGS. 1 to 3, and 6 to 8, each show for illustration a downwardly directed screw (29) arranged in the one most proximal screw hole (11), while an upwardly directed screw (30) is arranged in the other most proximal screw hole (11). In practice, normally either downwardly directed screws (29), as shown in FIGS. 14 and 16-17, or upwardly directed screws (30) are arranged in both most proximal screw holes (11).

In alternative embodiments, instead of said figure-of-eight shaped screw holes (11), separate screw holes may also be provided for downwardly directed screws and separate screw holes for upwardly directed screws. As a further alternative, only two or more proximal screw holes may be provided for downwardly directed screws, so that this fixation plate is then only used for operations in which the above-mentioned complications are feared, and an alternative fixation plate with only proximal screw holes for upwardly directed screws is used for operations where these complications are not expected.

The fixation plates (2) depicted may be attached both to a left humerus or to a right humerus of the human body. Alternatively, it is also possible to produce fixation plates (2) for a fixation system (1) according to this invention which are similar to the prior art, and only designed to be applied to the left humerus or only designed to be applied to a right humerus.

As well as said screw holes (5, 8) the fixation plate (2) is also provided with several suture holes (7). Suture threads (28) may be arranged in these suture holes (7).

Several suture holes (7) are provided for suture threads to be pulled through, as in the prior art, wherein these are pulled through tendons around the humeral head for securing the fixation plate (2).

An anchoring suture hole (10) is now also provided centrally in the fixation plate (2). This anchoring suture hole (10) is designed tunnel-like with a first inlet opening (40) at the upper edge of the head part (3), and a second inlet opening (41) centrally in the head part (3). Centrally between these two inlet openings (40, 41) is a screw hole (15) which opens into the tunnel-like cavity (14) of the anchoring suture hole (10). Via the inlet openings (40, 41), suture thread (28) can be introduced into the tunnel-like cavity (14), as can be seen in FIGS. 3, 14 and 17. By means of a setscrew (47) in the screw hole (15), this suture thread (28) can be adjustably and reversibly secured in this tunnel-like cavity (14).

A first bone anchoring element (9) of said bone anchoring elements (9, 33) of the fixation systems (1) depicted is provided in each case, to be anchored subchondrally in the apex (31) of the humeral head (32), medially from the foot plate of the major tubercle onto which the supra- and infraspinatus tendons (36) are inserted. Suture thread (28) is attached to this first bone anchoring element (9) and is inserted through the supra- and infraspinatus tendon (36) and secured in the anchoring suture hole (10) just described.

A second bone anchoring element (33) of said bone anchoring elements (9, (33) of the fixation systems (1) depicted is in each case designed to be anchored subchondrally, medially from the minor tubercle foot plate to which the subscapularis tendon is inserted. Suture thread (28) is attached to this bone anchoring element (33), inserted through the subscapularis tendon insertion (37) and secured in a second anchoring suture hole (17) in a side arm (16).

The side arm (16) is for this releasably attachable to the head part (3) of the fixation plate (2) and thus bridges the bicipital groove (45) so as to leave the biceps tendon unobstructed. In the embodiments depicted, the side arm (16) is attached at the front to the fixation plate (2). In alternative embodiments, this side arm (16) may also be attached at the rear to the fixation plate (2).

In each case, a tunnel-like cavity (17) is provided in this side arm (16) and has two inlet openings (42, 43) for insertion of the suture thread (28). A screw hole (44) is arranged transversely to this tunnel-like cavity (17) and opens into the tunnel-like cavity (17). Via the inlet opening (42, 43), the suture thread (28) can be introduced into the tunnel-like cavity (17), as can be seen in FIGS. 8, 14, 16 and 17. By means of a setscrew (48) in the screw hole (44), this suture thread (28) can be adjustably and reversibly secured in this tunnel-like cavity (17).

To attach the side arm releasably to the head part (3), this side arm (16) is in each case provided with a fixing body (18).

In the first embodiment depicted, this fixing body (18) extends over the complete width of the head part (3) and is attached on either side of this head part (3).

In the second embodiment depicted, the front face of this head part (3) is provided on either side with a recess (50) corresponding to the fixing body (18), in which the fixing body (18) can be arranged for fixing to the fixation plate (2). In this embodiment, the side arm (16) is designed symmetrically so that this can be attached either on the left to the fixation plate (2) as shown, or twisted through 180° on the right to the fixation plate (2).

In order to attach the fixing body (18) to the fixation plate (2), this fixing body (18) in both embodiments is provided with attachment pins (20) which can be inserted in suture holes (7) which are configured as attachment holes (35).

Also, both the fixing body (18) and the head part (3) may be provided with one or more corresponding fixing screw holes (38, 39), through which one or more screws may be introduced for screwing the fixing body (18) to the head part (3).

In the first embodiment, the fixing screw holes (39) in the head part (3) are here provided on opposite side edges of the head part (3). In the second embodiment, such a fixing screw hole (39) is provided in each of said recesses (50).

In the first embodiment, the fixing body (18) is provided with a cutout (21) to allow the unobstructed insertion of the most proximal angularly stable screws (24) in the head part (3).

The bone anchoring elements (9) may assume any form known from the prior art. One example of such bone anchoring elements suitable for this is known under the name Lupine® DePuy Synthes. As used herein, the terms foot plate or footplate are equivalent to the term footprint.

The invention claimed is:

1. Fixation plate for fixing to a proximal humerus,
comprising a head part and a shaft part adjoining the head part, wherein the head part is designed to be attached distally from the foot plate of the major tubercle of the humerus, comprising:
first screw holes each with internal screw thread for insertion of angularly stable screws therein; and
suture holes for insertion of suture material therein;
and wherein the shaft part is designed to be attached to the humeral shaft and for this is provided with second screw holes for insertion of fixing screws therein, characterized in that one of the suture holes is provided as an anchoring suture hole for anchoring thereto, by means of suture material, a bone anchoring element attached in the apex of the humeral head, and that two first screw holes arranged furthest from the shaft part are provided as upper screw holes for insertion therein of a downwardly directed screw; characterized in that the anchoring suture hole is provided for adjustably arranging suture material therein; and characterized in that the anchoring suture hole comprises a tunnel-like cavity, through which the suture material can be inserted and which is provided with adjustment means for adjustably securing the suture material in the tunnel-like cavity.

2. Fixation plate according to claim 1, characterized in that the anchoring suture hole is provided for releasably arranging the suture material therein.

3. Fixation plate according to claim 1, characterized in that the anchoring suture hole is arranged centrally in the head part.

4. Fixation plate according to claim 1, characterized in that internal screw thread of each of two or more upper screw holes comprises a longitudinal axis which is arranged at a downward angle between 10° and 35° relative to a horizontal plane.

5. Fixation plate according to claim 4, characterized in that the two or more upper screw holes are each provided with a second internal screw thread which comprises a second longitudinal axis which is arranged at an upward angle of between 10° and 35° with respect to the horizontal plane.

6. Fixation plate according to claim 4, characterized in that the two or more upper screw holes are each substantially designed in a figure-of-eight form with a upper inlet opening and a lower inlet opening, and that the upper inlet opening is provided with the first said internal screw thread, and the lower inlet opening is provided with the second internal screw thread.

7. Fixation plate according to claim 1, characterized in that on its side away from the head part, the shaft part is provided with an edge which is concave so as to form a free cavity centrally below the shaft part.

8. Set of a fixation plate according to claim 1, comprising a side arm which is releasably attachable to the head part and the side arm is provided with a second anchoring suture hole, in order to anchor the side arm medially to the minor tubercle by means of suture material and a second bone anchoring element.

9. Set according to claim 8, characterized in that the second anchoring suture hole is designed for adjustable insertion of the suture material therein.

10. Set according to claim 8, characterized in that the side arm is provided with a fixing body for fixing said side arm to the head part.

11. Set according to claim 10, characterized in that the head part is provided with a recess in which the fixing body may be arranged for fixing the fixing body to the head part.

12. Set according to claim 10, characterized in that the fixing body is provided with attachment pins which can be inserted in said suture holes which are configured as attachment holes for fixing the fixing body to the head part.

13. Method for treating a shoulder fracture, comprising attaching a fixation plate according to claim 1 to a proximal humerus, placing the head part distally from the foot plate of the major tubercle of the humerus, attaching the shaft part to the humeral shaft by means of fixing screws in the second screw holes, inserting two angularly stable screws, each pointing downward, in the first upper screw holes providing a bone anchoring element with suture material, attaching the bone anchoring element subchondrally to the apex of the humeral head, conducting the suture material through a supra- and infraspinatus tendon insertion site, and securing the suture material in the anchoring suture hole.

14. Set comprising:
i.) a fixation plate for fixing to a proximal humerus, comprising a head part and a shaft part adjoining the head part, wherein the head part is designed to be attached distally from the foot plate of the major tubercle of the humerus, comprising:
first screw holes each with internal screw thread for insertion of angularly stable screws therein; and
suture holes for insertion of suture material therein;
and wherein the shaft part is designed to be attached to the humeral shaft and for this is provided with second screw holes for insertion of fixing screws therein, characterized in that one of the suture holes is provided as an anchoring suture hole for anchoring thereto, by means of suture material, a bone anchoring element attached in the apex of the humeral head, and that two first screw holes arranged furthest from the shaft part are provided as upper screw holes for insertion therein of a downwardly directed screw; and
ii.) a side arm which is releasably attachable to the head part and the side arm is provided with a second anchoring suture hole, in order to anchor the side arm medially to the minor tubercle by means of suture material and a second bone anchoring element.

* * * * *